United States Patent [19]
Pal et al.

[11] Patent Number: 5,594,008
[45] Date of Patent: Jan. 14, 1997

[54] PYRROLIDINE DERIVATIVES INHIBITORS OF LEUKOTRIENE BIOSYNTHESIS

[75] Inventors: Kollol Pal, New Milford; Mark Behnke, Danbury; Julian Adams, Ridgefield, all of Conn.

[73] Assignee: Boehringer Ingelheim Pharmaceuticals, Inc., Ridgefield, Conn.

[21] Appl. No.: 362,373

[22] Filed: Dec. 22, 1994

Related U.S. Application Data

[63] Continuation of Ser. No. 143,270, Oct. 26, 1993, abandoned.

[51] Int. Cl.⁶ .................. A61K 31/44; C07D 213/06
[52] U.S. Cl. .................. 514/338; 514/375; 546/271.7; 546/276.4; 548/222
[58] Field of Search .................. 546/270; 514/338, 514/375; 548/222

[56] References Cited

FOREIGN PATENT DOCUMENTS 667649  10/1988  Switzerland .

OTHER PUBLICATIONS

Brunner et al CA 110 (21) 192821e 1988.

*Primary Examiner*—Amelia Owens
*Attorney, Agent, or Firm*—R. P. Raymond; M-E. M. Devlin; A. R. Stempel

[57] ABSTRACT

2-(1-pyrrolidino)-benzoxazoles of general formula

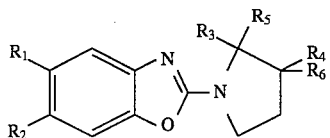

Formula 1 are disclosed which are inhibitors of leukotriene biosynthesis.

9 Claims, No Drawings

PYRROLIDINE DERIVATIVES INHIBITORS OF LEUKOTRIENE BIOSYNTHESIS

This is a continuation of application Ser. No. 08/143,270, filed Oct. 26, 1993, now abandoned.

BACKGROUND OF INVENTION

Leukotrienes (LTs) are potent pro-inflammatory mediators produced by the metabolism of arachidonic acid. They are believed to have a critical role in mediating the inflammatory response and consequently may be involved in the etiology of several diseases including asthma, rheumatoid arthritis, inflammatory bowel disease, and psoriasis. Therefore, the compounds of this invention, which inhibit the biosynthesis of the LTs, have potential use in the treatment of these diseases.

The biosynthesis of leukotrienes and their pathophysiology have been well documented. Many investigators have been seeking to block the pathophysiological effects of the leukotrienes, either by blocking their biosynthesis or by blocking their activity at the receptor level. Two recent reviews (J. H. Musser and A. F. Kreft. *J. Med. Chem.*, 1992, 35, 2501 and A. Shaw and R. D. Krell *J. Med. Chem.*, 1991, 34, 1235) describe the status of research in these areas, including results of clinical trials. Results of clinical trials such as those cited in these articles support the concept that agents which block the biosynthesis or activity of the leukotrienes will be useful in asthma and possibly other inflammatory diseases mentioned above.

THE INVENTION

This invention relates to inhibitors of leukotriene biosynthesis. In particular, this invention relates to novel 2-(1-pyrrolidino)-substituted benzoxazoles and pharmaceutically acceptable salts thereof, methods for preparing these compounds, to pharmaceutical compositions containing these compounds, and to the use of these compounds in the treatment of diseases in which inflammation and arachidonic acid metabolism have been implicated. These compounds may be racemic or may be a pure enantiomer, and the substitution on the pyrrolidine may be of either cis or trans configuration.

This invention relates to novel 2-(1-pyrrolidino)-benzoxazoles of the general formula

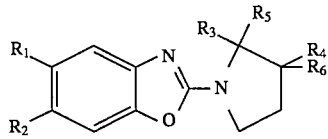

Formula 1 wherein $R_1$ and $R_2$ are each independently hydrogen, $C_1$–$C_6$ alkyl, —$CX_3$ wherein X is halo, $C_3$–$C_6$ cycloalkyl, halogen, nitrile, $C_1$–$C_6$ alkoxy, —$CO_2R_7$ (where $R_7$ is H, $C_1$–$C_6$ alkyl), —$C(O)NR_8R_9$ (where $R_8$ and $R_9$ are H, $C_1$–$C_3$ alkyl, methoxy), —$NO_2$, —$NR_{10}R_{11}$ (where $R_{10}$ and $R_{11}$ are H, $C_1$–$C_3$ alkyl), —$SO_2$-phenyl-$CH_3$, —$C(O)R_{12}$ (where $R_{12}$ is $C_1$–$C_6$ alkyl), $R_3$ is $C_1$–$C_6$ alkyl, $C_3$–$C_6$ cycloalkyl, an optionally substituted phenyl ring $C_6H_4Z$ [where Z is halogen, $C_1$–$C_3$ alkoxy, $C_1$–$C_4$ alkyl], —$NR_{13}R_{14}$ (where $R_{13}$ $R_{14}$ are $C_1$–$C_3$ alkyl), a five or six membered heteroaromatic ring with one, two, or three heteroatoms which may include nitrogen, oxygen, or sulfur, $R_4$ is $C_1$–$C_6$ alkyl, $C_3$–$C_6$ cycloalkyl, an optionally substituted phenyl ring $C_6H_6Z$ [where Z is as hereinabove defined], $R_5$ is hydrogen or $C_1$–$C_4$ alkyl and $R_6$ is $C_1$–$C_3$ alkyl or hydrogen. The compounds may be racemic or a pure enantiomer; however, a pure enantiomer may be more preferred. The substitution on the cyclic amine ring may be of either cis or trans configuration.

A subgeneric aspect of the invention comprises compounds of Formula 1 wherein $R_1$ is $C_1$–$C_3$ alkyl, halogen, or perhalocarbon, $R_3$ is 2-, 3-, or 4-pyridyl, $R_4$ is cyclohexyl or 4-fluorophenyl, and both $R_5$ and $R_6$ are hydrogen. The configuration of the $R_3$ and $R_4$ substituents can be either the cis or trans orientation; the trans configuration is preferred. The compounds may be racemic or a pure enantiomer; however, a pure enantiomer may be more preferred.

Especially preferred compounds of Formula 1 are those wherein $R_1$ is halogen, $R_3$ is 2-pyridyl, $R_4$ is 4-fluorophenyl, 4-methoxyphenyl, 4-methylphenyl, 3-fluorophenyl, 4-chlorophenyl, 3-chlorophenyl, 3-methoxyphenyl, and 3-methylphenyl, and both $R_5$ and $R_6$ are hydrogen.

SYNTHESIS OF COMPOUNDS AND THEIR SALTS

The compounds of this invention can be prepared by a number of different methods or obvious modifications thereof. Methods A through F described below are illustrative of the methods for preparing the compounds.

METHOD A

In general, compounds of Formula 1 may be prepared by reaction of an appropriately substituted 2-chlorobenzoxazole of Formula 3 wherein $R_1$ and $R_2$ are as described above with an appropriately substituted pyrrolidine of Formula 2 wherein $R_3$, $R_4$, $R_5$ and $R_6$ are as described above. The reaction is generally carried out in the presence of an acid scavenger such as triethylamine, diisopropylethylamine, or NaOH. The synthesis of appropriately substituted 2-chlorobenzoxazoles has been previously described in the literature. The coupling reaction may be carried out in neutral solvents such as methylene chloride, dioxane, toluene, or DMSO and reaction conditions (solvent, temperature, reaction time) will depend on the particular reactants. The following is an example.

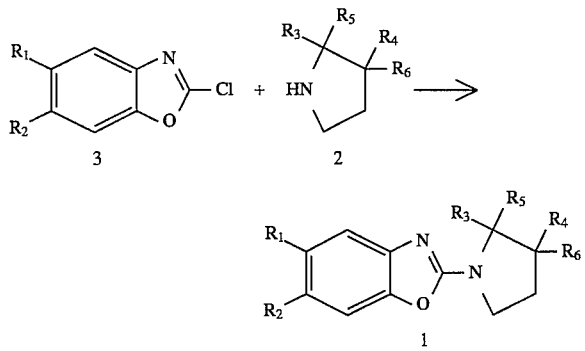

METHOD B

The cis disubstituted pyrrolidines can be prepared by a number of methods as described below. A key intermediate in the preparation of the cis pyrrolidines is the cyclic imine 7. Reduction of this imine will be directed by the C-3 substituent to the less hindered face of the imine resulting in the formation of the desired cis compounds. In METHOD B, the key cyclic imine can be prepared from a suitably functionalized ketone in a three-step, one-pot operation. Lithiation of the ketone 4, wherein $R_3$, $R_4$, $R_5$ and $R_6$ are as described above, with a hindered base such as LDA, LDEA or LTMP followed by transmetallation with $ZnCl_2$ produces the enolate 5 where M is zinc. Reaction of this enolate with nitroethylene affords the intermediate nitro compounds (6, X is $NO_2$). Reduction of the nitro compound can be effected by a number of protocols which have been described in the literature (for a summary see R. C. Larock, *Comprehensive Organic Transformation*, VCH Publishers, Inc. 1989). Some of these include metal reductions with reagents such as $FeCl_3$ and $SnCl_4$. Transfer hydrogenation methods have also been reported to reduce nitro compounds. Hydride reagents have also been reported to reduce nitro groups, but a competing reaction which has been often observed is the reduction of the ketone as well. Reduction with Raney nickel in an alcoholic solution under a hydrogen atmosphere produces the intermediate amine (6, X is $NH_2$) which immediately cyclizes to imine 7. Under the hydrogenation conditions used to reduce the nitro group, the cyclic imine 7 can be further reduced to the desired amine. Alternatively, the imine may also be isolated and then reduced using a variety of reducing agents such as $NaBH_4$, $NaBH_3CN$ or LAH. The stereoselectivity of the reduction may depend upon the reducing agent, stoichiometry of reagents and the reaction conditions which are employed. Temperature and solvent effects are known to effect the stereoselectivity of the reduction.

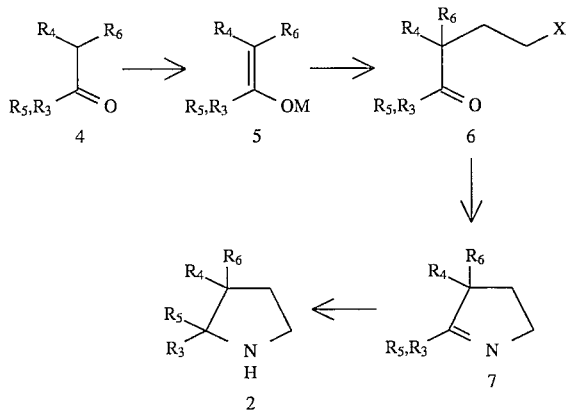

Other approaches which involve a suitably substituted 4-aminoketone intermediate can also be used to make the key pyrroline intermediates which will then afford the cis substituted pyrrolidines upon reduction. In place of the nitroethylene, a number of 2-aminoethyl equivalent alkylating agents can also be employed. For example, reaction of the enolate 5 with a 2-halo-acetonitrile will produce an intermediate cyanoketone which can then be reduced to either the pyrroline or pyrrolidine system. Other electrophiles include various 2-halo-aminoethyl derivatives with protecting groups on the nitrogen which are capable of withstanding the strongly basic reaction conditions needed for the alkylation step. A Boc or Cbz protecting group on the nitrogen may be compatible with these reactions. For example, alkylation of the ketone 4 with a suitably protected 2-aminoethyl halide will generate an N-protected system 6 (X is a N-protected group). Removal of the protecting group results in the spontaneous cyclization to the imine which can then be reduced to the cyclic amine. Alternatively, an alkylating agent may be used which will introduce a suitable leaving group (X is halide, p-toluenesulfonate) which can then be displaced with an amine equivalent. An azide group, which can later be reduced to an amine, can also be used in the place of a protected amine derivative.

METHOD C

A number of known literature methods can also be used to prepare different cyclic imines 7 wherein $R_3$, $R_4$, $R_5$ and $R_6$ are as described previously. These can then be further elaborated before reduction to the desired cis substituted amines. For example, an intramolecular alkylation strategy utilizes the reaction of an appropriate halonitrile with a Grignard reagent to generate 2-substituted pyrrolines (A. E. Kemppanien, M. J. Thomas, P. J. Wagner *J. Org. Chem.*, 1976, 41, 1294). These pyrrolines can be selectively functionalized at the C-3 position through a metallation and alkylation protocol. This strategy complements Method A in that it allows the preparation of C-3 substituted pyrrolines which are not amenable to the previously described conditions.

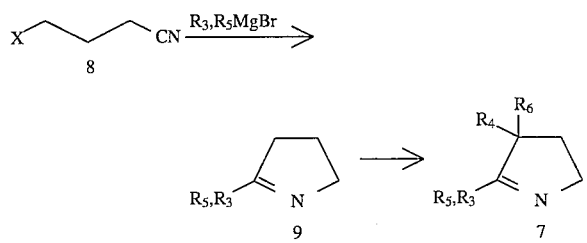

METHOD D

The acid catalyzed thermolysis of appropriately substituted cyclopropyl nitriles has also been reported to generate pyrrolines (R. V. Stevens, M. C. Ellis *Tetrahedron Lett.*, 1964, 5185). The appropriate cyclopropylnitriles can be easily prepared from readily available acetonitrile derivatives via alkylation with 1-bromo-2-chloroethane. Reaction of the nitrile with Grignard reagents, as described above, results in the addition of the Grignard to the nitrile moiety. These can be hydrolyzed to the imines which have been shown to undergo acid catalyzed thermolysis to the desired 23-disubstituted pyrrolines.

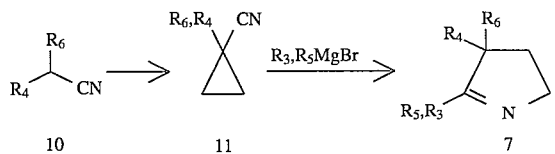

METHOD E

The trans pyrrolidines can be obtained as minor products in the hydride reductions discussed above. Reaction conditions can also be modified to increase the ratio of the trans adduct. However, in all cases the cis isomer is still the major component of the reaction mixture. These modifications include the use of higher temperatures or more reactive hydride reagents in the reduction step.

Alternatively, the trans pyrrolidines can be prepared in a stereoselective manner using a number of different literature approaches. Method E involves the reaction of a 2-aza-allyl anion with an appropriately substituted styrene derivative to produce the desired pyrrolidine directly (W. H. Pearson, D. P. Szura, M. J. Povitch *J. Am. Chem. Soc.*, 1992, 114, 1329). The desired 2-aza-allyl anion may be generated by a number of methods. The direct deprotonation of an appropriately substituted Schiff base has been reported to generate the desired anion, Conversely, a transmetallation reaction of a stannane to the lithiated species has also been reported to generate the desired aza-allyl anion. This intermediate can then be trapped with an appropriately substituted dipolarophile to produce the desired pyrrolidine system. The major product of this reaction is the desired 2,3-disubstituted trans pyrrolidine isomer. These two isomers are readily separable by column chromatography, and can be purified at either the pyrrolidine stage or after coupling with an appropriate 2-chlorobenzoxazole.

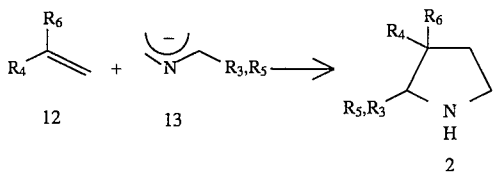

METHOD F

Azomethine ylids, which are more reactive as well as more stable than 2-aza-allyl anions, have also been reported to undergo reaction with activated olefins to produce pyrrolidines (A. Padwa, W. Dent *J. Org. Chem.*, 1987, 52, 235). Method F involves the reaction of appropriately substituted azomethine ylids, generated using a number of literature protocols, with a variety of styrenes and reactive olefins to generate a mixture of 2,3 and 2,4 trans substituted pyrrolidines from which the desired product can be obtained by chromatographic separation.

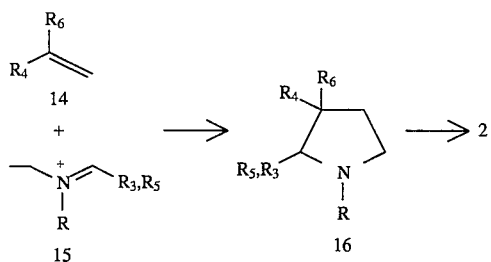

EXAMPLES

The following examples further illustrate the present invention and will enable others skilled in the art to understand it more completely. It should be understood, however, that the invention is not limited to the particular examples given below.

Example 1 cis-+/−-5-Chloro-3-(4-fluorophenyl)-2-(2-pyridyl)-pyrrolidin-1-yl-benzoxazole

A flame-dried 2 L three-necked round bottomed flask was charged with finely divided magnesium (13.4 g, 0.55M). A solution of 4-fluorobenzyl chloride (80 g, 0.55M) in 400 mL ether was added to the reaction flask over 45 min at a rate to maintain a gentle reflux. The resulting dark grey reaction mixture was heated at reflux for an additional 24 h. A solution of 2-cyanopyridine (57.6 g, 0.55M) in 400 mL ether was then added over 15 min to the reaction mixture at a rate to maintain a steady reflux and the resulting green colored mixture was heated at reflux for an additional 24 h. The reaction mixture was cooled to room temperature, quenched by the addition of 800 mL methanol, and then carefully acidified to pH 2 with concentrated HCl. After stirring for 1 h, the reaction mixture was extracted with two 500 mL portions ethyl acetate. The aqueous portion was then made alkaline with 40% aqueous KOH solution, washed with three 500 mL portions ethyl acetate, and the combined organic phase was washed with 250 mL saturated sodium chloride solution, dried over magnesium sulfate, filtered, and concentrated to obtain a brown residue which was recrystallized from petroleum ether to obtain 52.47 g (44%) of the desired 2-(3(4-fluorophenyl)-2-oxo)-pyridine as a yellow solid. mp 55° C.

To a solution of diisopropylamine (35.8 mL, 0.26M) in 50 mL THF cooled to −78° C. was added a solution of n-BuLi (102.2 mL, 2.5M in hexanes, 0.26M) and the resulting clear colorless solution was allowed to stir at that temperature for 15 min. To this solution was then added a solution of the above ketone (50 g, 0.23M) in 250 mL THF and the yellow solution was allowed to stir at −78° C. for 1 hour. A solution of $ZnCl_2$ (465 mL, 0.5M in THF, 0.23M) was then added dropwise to the dark yellow solution followed by warming of the reaction mixture to 0° C. The resulting pale yellow solution was then cooled to −78° C., freshly distilled nitroethylene (18.67 g, 0.23M) was added dropwise, and the reaction was allowed to warm to −10° C. over 36 hours. A 30 mL portion of saturated ammonium chloride solution was added to the reaction followed by the addition of 500 mL ethyl acetate. The organic phase was washed with 200 mL portions of water and saturated sodium chloride solution, dried over magnesium sulfate, filtered, and concentrated to a brown solid which was chromatographed on silica gel with methylene chloride to obtain 20 g (30%) of the desired 2-(3-(4-fluorophenyl)-3-(2-nitroethyl)-2-oxo)-pyridine as a yellow oil.

This material (20 g, 0.07M) was dissolved in 600 mL ethanol and transferred to a Parr bottle to which was added 10 g Raney nickel. The resulting slurry was shaken under a hydrogen atmosphere (50 psi) for 27 h, filtered through a pad of Celite, and concentrated to afford a pale yellow oil which was then chromatographed on silica gel with methylene chloride to obtain 9.6 g (58%) of the desired $\Delta^1$-3-(4-fluorophenyl)-2-(2-pyridyl)-pyrroline as a pale yellow oil.

The crude pyrroline (6 g 0.025M) was dissolved in 100 mL methanol and cooled to 0° C. Sodium cyanoborohydride (1.57 g, 0.025M) was added to the solution and then the reaction mixture was adjusted to pH 3 with aqueous 2N HCl solution and maintained at that level for 1 hour. The resulting yellow solution was neutralized with aqueous 1N sodium hydroxide solution and extracted with 250 mL ethyl acetate. The organic layer was washed with 100 mL portions of water and saturated sodium chloride solution, dried over magnesium sulfate, filtered, and concentrated to obtain 5.9 g (100%) of the desired 3-(4-fluorophenyl)-2-(2-pyridyl)-pyrrolidine which was used immediately in the ensuring reaction.

The crude pyrrolidine (5.9 g, 0.025M) was dissolved in 100 mL 1,4-dioxane containing N,N-diisopropylethylamine (435 mL, 0.025M). Then 2,5-dichlorobenzoxazole (4.7 g, 0.025M) was added and the resulting yellow solution was heated at reflux for 2 hours, cooled to room temperature and diluted with 250 mL ethyl acetate. The reaction mixture was washed with 200 mL portions of water and saturated sodium chloride solution, dried over magnesium sulfate, filtered and concentrated to obtain a yellow oil. Chromatography on silica gel with methylene chloride-methanol resulted in 4.6 g (47%) of the desired cis-+/−-5-chloro-3-(4-fluorophenyl)-2-(2-pyridyl-pyrrolidin- 1-yl-benzoxazole, mp 149°–150° C.

Example 2

$\Delta^1$-3-ethyl-2-phenyl-pyrroline

To a solution of phenylmagnesium bromide (16.9 mL, 3M in ether, 50.7 mM) in 100 mL ether was added over 45 min a solution of 4-chlorobutyronitrile (5 g, 483 mM) in 100 mL ether. The resulting white slurry was then heated at reflux for 5 hours, 200 mL xylenes were added to the reaction mixture, and the ether was removed by distillation. The resulting reaction mixture was then heated at 130° C. for 3 hours and the tan colored slurry was cooled to room temperature and washed with a 100 mL portion of saturated ammonium chloride solution. The aqueous phase was washed with 200 mL ethyl acetate, and the combined organic phase was then washed with 100 mL portions of saturated sodium bicarbonate solution and saturated sodium chloride solution, dried over magnesium sulfate, filtered, and concentrated to obtain a yellow oil which was then distilled at 80°–82° C. at 1 mm Hg to obtain 4.97 g (71%) of the $\Delta^1$-2-phenyl-pyrroline.

A solution of lithium diisopropylamide was prepared by the addition of a solution of nBuLi (1.52 mL, 2.5M in hexanes, 3.8 mM) to a solution of diisopropylamine (0.53 mL, 3.8 mM) in 12 mL THF which was cooled to −78° C. To this solution was added a solution of the above mentioned pyrroline (0.5 g, 3.4 mM) in 3 mL THF and the resulting yellow solution was allowed to stir at −78° C. for one hour. The reaction mixture was warmed to 0° C. and then recooled to −78° C. Ethyl iodide (0.5 mL, 6.25 mM) was added to the reaction mixture which was then allowed to warm to room temperature over one hour. The addition of 1 mL of a saturated ammonium chloride solution was followed by the addition of 50 mL ethyl acetate. The organic layer was sequentially washed with 25 mL water and saturated sodium chloride solution, dried over magnesium sulfate, filtered and concentrated to a dark yellow oil which was then chromatographed on silica gel with methylene chloride and methanol to obtain 0.374 g (58%) of the desired $\Delta^1$-3-ethyl-2-phenyl-pyrroline.

Example 3

$\Delta^1$-2-phenyl-3-(3-pyridyl)-pyrroline

To a solution of 3-pyridyl-1,1-cyclopropylnitrile (1.5 g, 10.4 mM) in 50 mL ether was added a solution of phenyl-magnesium bromide (4.3 mL, 3M in ether, 13 mM) and the resulting dark red slurry was allowed to heat at reflux for 3 hours. After cooling the reaction mixture to room temperature, sodium sulfate decahydrate (9.4 g, 29.1 mM) was added and the reaction mixture was stirred for one hour. The solids were filtered, washed with ether, and the combined organic phase was concentrated to obtain 2.47 g of a yellow oil which was then dissolved in 50 mL toluene. A small amount of ethereal HCl was added, and the reaction mixture was then heated to reflux for 2 hours. After allowing the reaction mixture to cool to room temperature, it was washed with 100 mL portions of saturated sodium bicarbonate solution, saturated sodium chloride solution, dried over magnesium sulfate, filtered, and concentrated to a yellow oil. Column chromatography on silica gel with ethyl acetate and hexanes afforded 1.68 g (73%) of a white solid.

Example 4 trans-+/−-5-Chloro-3-(4-fluorophenyl)-2-(2-pyridyl)-pyrrolidin-1-yl-benzoxazole

A thick wall pressure bottle was charged with 40 mL of 40% aqueous methylamine solution and 2-pyridine carboxaldehyde (22.5 g 0.21M) in 50 mL methanol. The bottle was sealed and the reaction mixture was stirred at room temperature for 17 hours. The orange colored solution was concentrated, the resulting oil was dissolved in 100 mL ethyl acetate, dried over magnesium sulfate, filtered and concentrated to produce 21.1 g (83%) of yellow oil. A solution of diisopropylamine (25.2 mL, 0.18M) in 100 ml THF was cooled to −78° C., nBuLi (2.5M in hexanes, 72 mL, 0.18M) was added dropwise, and the resulting solution was stirred for 15 minutes. A solution of the Schiff base (19.67 g, 0.16M) in 400 mL THF was added dropwise to the reaction mixture at −78° C., and the dark red solution was stirred at that temperature for 1 hour. A solution of 4-F-styrene (20 g, 0.16M) in 100 mL THF was added over 15 min to the reaction and then allowed to warm to 25° C. over 3 hours. The reaction mixture was quenched by the addition of 25 mL of a saturated ammonium chloride solution and then diluted with 500 mL of ethyl acetate. The organic layer was separated, washed with 100 mL portion of water and saturated sodium chloride solution, dried over magnesium sulfate, filtered and concentrated to obtain 43.53 g of a yellow oil which was then chromatographed on silica gel with methylene chloride-methanol-ammoniumhydroxide to obtain 21.23 g (54%) of the desired trans-2-(2-pyridyl)-3-(4-fluorophenyl)-pyrrolidine. A solution of the pyrrolidine (14.2 g, 0.059M), 2,5-dichlorobenzoxazole (11 g, 0.059M), and N,N-diisopropylethylamine (10.2 mL, 0.059M) in 300 mL 1,4-dioxane was heated to reflux and stirred at that temperature for one hour. The resulting dark brown solution was cooled to room temperature, diluted with 400 mL ethyl acetate and the organic phase was washed with 100 mL portions of water and saturated sodium chloride solution, dried over magnesium sulfate, filtered, and concentrated to obtain 27 g of a yellow oil. The oil was chromatographed on silica gel with methylene chloride-methanol to obtain 19.5 g (85%) of the desired product as a viscous yellow oil which was dissolved in 100 mL ether and then 100 mL of a HCl saturated ethereal solution was added resulting in the formation of a white precipitate. The solid was filtered, washed with ether and recrystallized from ethanol-petroleum ether to obtain 17.5 g of the desired product as the dihydrochloride salt. The mother liquor afforded an additional 3.75 g of the product upon concentration and recrystallization for a combined yield of 21.25 g (92%), mp 160°–2° C.

DESCRIPTION OF ASSAYS

The inhibition of leukotriene biosynthesis is measured by determining whether and to what extent test compounds can inhibit $LTB_4$ production from endogenous arachidonic acid in human peripheral blood leukocytes. To a 48-well tissue culture plate was added a solution of the test compound followed by addition of human polymorphonuclear leukocytes isolated from peripheral blood at a density of $1.5 \times 10^6$ cells/well. Culture plates were preincubated for approximately fifteen minutes with shaking at about 28° C. Cells were stimulated with calcium inonophore A23187 at a final concentration of 2.5 µM for an additional 10 min. The reaction was terminated by the addition of an EGTA solution (10 mM final concentration) followed by centrifugation at 1500 rpm at about 10° C. Supernatants were stored at about −70° C. $LTB_4$ levels were determined by RIA using a commercially available kit. Nonlinear regression analysis was used to calculate percentage of inhibition values. The following table shows percent inhibition of $LTB_4$ by compounds of this invention at the test concentration of one micromolar.

| No. | $R_1$ | $R_3$ | $R_4$ | C/T | MP | % 1 µM |
|---|---|---|---|---|---|---|
| 1 | 5-Cl | Ph | Ph | C | 185–6 | 82 |
| 2 | 5-Cl | 2Py | 4FPH | C | 149–50 | 80 |
| 3 | 5-iPr | Bn | H | | OIL | 76 |
| 4 | 5-Cl | Bn | H | | OIL | 67 |
| 5 | 5-Cl | $CO_2Me$ | H | | 79–81 | 87 |
| 6 | 5-Cl | 5MeTh | 3ClPh | C | OIL | 80 |
| 7 | 5-iPr | Et | Ph | C | OIL | 83 |
| 8 | 5-MeO | Et | Ph | C | OIL | 84 |
| 9 | 5-iPr | 4BrPh | Pr | C | OIL | 100 |
| 10 | 5-MeO | 4BrPh | Pr | C | OIL | 87 |

-continued

| No. | $R_1$ | $R_3$ | $R_4$ | C/T | MP | % 1 μM |
|---|---|---|---|---|---|---|
| 11 | 5-iPr | Ph | H | | OIL | 59 |
| 12 | 5-Cl | Ph | H | | 142–3 | 30 |
| 13 | 5-iPr | 5MeTh | 3ClPh | C | OIL | 63 |
| 14 | 5-iPr | Ph | Me | T | OIL | 100 |
| 15 | 5-iPr | Ph | Me | C | 108–10 | 89 |
| 16 | 5-iPr | Ph | Pr | T | OIL | 78 |
| 17 | 5-iPr | Ph | Pr | C | OIL | 76 |
| 18 | 5-Cl | Ph | $CH_2SCH_3$ | T | OIL | 62 |
| 19 | 5-Cl | Ph | $CH_2SCH_3$ | C | 140–2 | 49 |
| 20 | 5-iPr | Ph | Et | T | 82–4 | 61 |
| 21 | 5-iPr | Ph | Et | C | OIL | 74 |
| 22 | 5-iPr | Ph | Et | C | 87–8 | |
| 23 | 5-Cl | 2Py | 4FPh | T | OIL | 100 |
| 24 | 5-MeO | 2Py | 4FPh | C | 49–51 | 45 |
| 25 | 5-iPr | Ph | Ph | T | OIL | 85 |
| 26 | 5-iPr | Ph | Ph | C | 153–5 | 67 |
| 27 | 5-Cl | Ph | Ph | T | FOAM | 81 |
| 28 | 5-Cl | Ph | 3Py | T | 77–9 | 65 |
| 29 | 5-Cl | Ph | 3Py | C | 181–3 | 48 |
| 30 | 5-Cl | Ph | Ph,Me | | 66–7 | 93 |
| 31 | 5-Cl | Ph | Me,Ph | | 133–5 | 80 |
| 32 | 5-Cl | 2Py,Me | 4FPh | | 80–2 | 30 |
| 33 | 5-Cl | $CO_2Me$ | Ph | T | 166–8 | 15 |
| 34 | 5-Cl | 2Py | $4CF_3Ph$ | T | OIL | 75 |
| 35 | 5-Cl | 2Py | 3,4MeOPh | T | OIL | 48 |
| 36 | 5-Cl | 2Py | Ph | T | OIL | 100 |
| 37 | 5-MeO | 2Py | Ph | T | OIL | 100 |
| 38 | 5-Cl | 2Py | Naph | T | OIL | 100 |
| 39 | 5-Cl | 2Thiop | 4FPh | C | 136–8 | 69 |
| 40 | 5-Cl | 2Thiop | 4FPh | T | 129–31 | 64 |
| 41 | 5-iPr | 2Py | 4FPh | T | 202–4 | 57 |
| 42 | 5-Cl | 2Py | CH | C | 184–6 | 97 |
| 43 | 5-Cl | 2Py | CH | t | 129–30 | 94 |
| 44 | 5-Cl | 2Py | 3ClPh | C | 151–2 | 84 |
| 45 | 5-Cl | 2Py | 3ClPh | T | RESIN | 91 |
| 46 | 5,6-diF | 2Py | 4F-Ph | T | 54–56 | 56 |
| 47 | 5-$CF_3$ | 2Py | 4F-Ph | T | 199–201 | 83 |
| 48 | 5-Cl | Ph | 4F-$PhCH_2$ | C | 164–166 | 64 |
| 49 | 5-Cl | Ph | 4F-$PhCH_2$ | T | RESIN | 87 |
| 50 | 5-Cl | 4F-Ph | 2Py | T | RESIN | 51 |
| 51 | 5-Cl | 4F-Ph | 2Py | C | RESIN | 67 |
| 52 | 5-Cl | 3-Py | 4F-Ph | C | RESIN | 4 |
| 53 | 5-Cl | 3-Py | 4F-Ph | T | RESIN | 79 |
| 54 | 5-$CF_3$ | 2Py | CH | C | 160–161 | 69 |
| 55 | 5-$CF_3$ | 2Py | CH | T | RESIN | 75 |
| 56 | 5-Cl | 2Py | 3Ph-OBn | T | OIL | 33 |
| 57 | 5-Cl | 2Py | 2-N-Me-Pyrrole | T | OIL | 78 |
| 58 | 5-Cl | 2Py | 2-Furan | T | OIL | 100 |
| 59 | 5-Cl | 2Py | 4-Me-thiazole | T | OIL | 54 |
| 60 | 5-Cl | Ph | SPh | T | OIL | 100 |
| 61 | 5-Cl | 2Py | 4MeOPh | T | OIL | 81 |
| 62 | 5-Cl | 2Py | 2MePh | T | OIL | 83 |
| 63 | 5-Cl | 2Py | 3-Me-Thiazole | T | OIL | 91 |
| 64 | 5-Cl | 2Py | 4MePh | T | RESIN | 98 |
| 65 | 5-Cl | 2Py | 3,4-diFPh | T | RESIN | 87 |
| 66 | 5-Cl | 2Py | 3-F-Ph | T | RESIN | 89 |
| 67 | 5-Cl | 2Py | 4-Eto-Ph | T | RESIN | 78 |
| 68 | 5-Cl | 2Py | 3-MeOPh | T | RESIN | 81 |
| 69 | 5-Cl | 2Py | 2-MeOPh | T | RESIN | 82 |
| 70 | 5-Cl | Ph | 3-$NO_2$-Ph | T | OIL | 76 |

What is claimed is:

1. A compound of formula 1

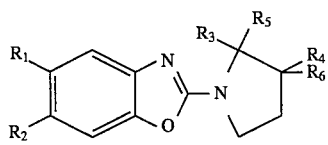

wherein $R_1$ and $R_2$, independently, are hydrogen, $C_1$–$C_6$ alkyl, —$CX_3$ wherein X is halo, $C_3$–$C_6$ cycloalkyl, halogen, nitrile, $C_1$–$C_6$ alkoxy, —$CO_2R_7$ where $R_7$ is hydrogen or $C_1$–$C_6$ alkyl, —$C(O)NR_8R_9$, where $R_8$ and $R_9$ are hydrogen, $C_1$–$C_3$ alkyl or methoxy, —$NO_2$, —$NR_{10}R_{11}$, where $R_{10}$ and $R_{11}$ are hydrogen or $C_1$–$C_3$ alkyl, —$SO_2$-phenyl-$CH_3$, or —$C(O)R_{12}$, where $R_{12}$ is $C_1$–$C_6$ alkyl, $R_3$ is $C_1$–$C_6$ alkyl, $C_3$–$C_6$ cycloalkyl, an optionally substituted phenyl group where the substituents are halo, $C_1$–$C_4$ alkyl, or $C_1$–$C_3$ alkoxy, 2-, 3- or 4-pyridyl, or —$NR_{13}R_{14}$, where $R_{13}$ and $R_{14}$ are $C_1$–$C_3$ alkyl, $R_4$ is $C_1$–$C_6$ alkyl, $C_3$–$C_6$ cycloalkyl, or an optionally substituted phenyl group where the substituents are halo, $C_1$–$C_4$ alkyl or $C_1$–$C_3$ alkoxy, $R_5$ is hydrogen or $C_1$–$C_4$ alkyl $R_6$ is hydrogen or $C_1$–$C_3$ alkyl in racemic form or a substantially pure enantiomer thereof.

2. The compound as recited in claim 1 wherein $R_1$ is $C_1$–$C_3$ alkyl, halogen or —$CX_3$ $R_2$ is hydrogen $R_3$ is 2-, 3- or 4-pyridyl, $R_4$ is cyclohexyl or 4-fluorophenyl and $R_5$ and $R_6$ are hydrogen.

3. The compound as recited in claim 2 wherein $R_1$ is halogen, $R_3$ is 2-pyridyl, $R_4$ is 4-fluorophenyl and both $R_5$ and $R_6$ are hydrogen.

4. The compound as recited in claim 1 where the $R_3$ and $R_4$ substituents are in the trans configuration.

5. A compound of formula 1

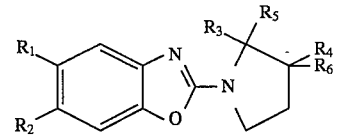

wherein $R_1$ is chloro $R_2$ is hydrogen $R_3$ is 2-pyridyl $R_4$ is 4-fluorophenyl and $R_5$ and $R_6$ are hydrogen, in racemic form or a substantially pure enantiomer thereof.

6. A compound of formula 1

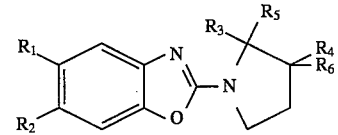

wherein $R_1$ is chloro $R_2$ is hydrogen $R_3$ is 2-pyridyl $R_4$ is 4-methoxyphenyl and $R_5$ and $R_6$ are hydrogen, in racemic form or a substantially pure enantiomer thereof.

7. A compound of formula 1

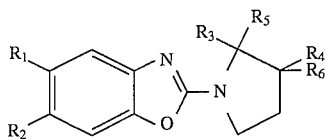

wherein $R_1$ is chloro $R_2$ is hydrogen $R_3$ is 2-pyridyl $R_4$ is 4-methylphenyl and $R_5$ and $R_6$ are hydrogen, in racemic form or a substantially pure enantiomer thereof.

8. A pharmaceutical composition of matter comprising a compound of formula 1

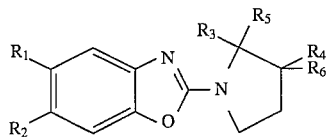

wherein $R_1$ and $R_2$, independently, are hydrogen, $C_1$–$C_6$ alkyl, —$CX_3$ wherein X is halo, $C_3$–$C_6$ cycloalkyl, halogen, nitrile, $C_1$–$C_6$ alkoxy, —$CO_2R_7$ where $R_7$ is hydrogen or $C_1$–$C_6$ alkyl, —$C(O)NR_8R_9$, where $R_8$ and $R_9$ are hydrogen, $C_1$–$C_3$ alkyl or methoxy, —$NO_2$, —$NR_{10}R_{11}$, where $R_{10}$ and $R_{11}$ are hydrogen or $C_1$–$C_3$ alkyl, —$SO_2$-phenyl-$CH_3$, or —$C(O)R_{12}$, where $R_{12}$ is $C_1$–$C_6$ alkyl, $R_3$ is $C_1$–$C_6$ alkyl, $C_3$–$C_6$ cycloalkyl, an optionally substituted phenyl group where the substituents are halo, $C_1$–$C_4$ alkyl, or $C_1$–$C_3$ alkoxy, 2-, 3- or 4-pyridyl, or —$NR_{13}R_{14}$, where $R_{13}$ and $R_{14}$ are $C_1$–$C_3$ alkyl, $R_4$ is $C_1$–$C_6$ alkyl, $C_3$–$C_6$ cycloalkyl, or an optionally substituted phenyl group where the substituents are halo, $C_1$–$C_4$ alkyl or $C_1$–$C_3$ alkoxy, $R_5$ is hydrogen or $C_1$–$C_4$ alkyl $R_6$ is hydrogen or $C_1$–$C_3$ alkyl in racemic form or a substantially pure enantiomer thereof, together with one or more pharmaceutically acceptable carriers or diluents.

9. A method of treating disease in a warm-blooded animal which disease is medicated by leukotriene biosynthesis which comprises administering to said animal a leukotriene biosynthesis inhibiting amount of a compound of formula 1

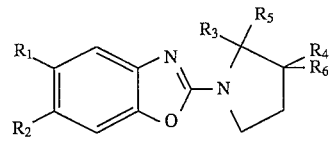

wherein $R_1$ and $R_2$, independently, are hydrogen, $C_1$–$C_6$ alkyl, —$CX_3$ wherein X is halo, $C_3$–$C_6$ cycloalkyl, halogen, nitrile, $C_1$–$C_6$ alkoxy, —$CO_2R_7$ where $R_7$ is hydrogen or $C_1$–$C_6$ alkyl, —$C(O)NR_8R_9$, where $R_8$ and $R_9$ are hydrogen, $C_1$–$C_3$ alkyl or methoxy, —$NO_2$, —$NR_{10}R_{11}$, where $R_{10}$ and $R_{11}$ are hydrogen or $C_1$–$C_3$ alkyl, —$SO_2$-phenyl-$CH_3$, or —$C(O)R_{12}$, where $R_{12}$ is $C_1$–$C_6$ alkyl, $R_3$ is $C_1$–$C_6$ alkyl, $C_3$–$C_6$ cycloalkyl, an optionally substituted phenyl group where the substituents are halo, $C_1$–$C_4$ alkyl, or $C_1$–$C_3$ alkoxy, 2-, 3- or 4-pyridyl, or —$NR_{13}R_{14}$, where $R_{13}$ and $R_{14}$ are $C_1$–$C_3$ alkyl, $R_4$ is $C_1$–$C_6$ alkyl, $C_3$–$C_6$ cycloalkyl, or an optionally substituted phenyl group where the substituents are halo, $C_1$–$C_4$ alkyl or $C_1$–$C_3$ alkoxy, $R_5$ is hydrogen or $C_1$–$C_4$ alkyl $R_6$ is hydrogen or $C_1$–$C_3$ alkyl in racemic form or a substantially pure enantiomer thereof.

* * * * *